United States Patent [19]

Sinofsky

[11] Patent Number: 4,852,567
[45] Date of Patent: Aug. 1, 1989

[54] LASER TIPPED CATHETER

[75] Inventor: Edward L. Sinofsky, Reading, Mass.

[73] Assignee: C. R. Bard, Inc., Murray Hill, N.J.

[21] Appl. No.: 146,341

[22] Filed: Jan. 21, 1988

[51] Int. Cl.$^4$ .............................................. A61B 17/36
[52] U.S. Cl. ................................................. 128/303.1
[58] Field of Search ..................... 128/303.1, 395–398; 372/41, 75, 92, 99; 307/425

[56] References Cited

U.S. PATENT DOCUMENTS

| | | | |
|---|---|---|---|
| 3,471,215 | 10/1969 | Snitzer | 350/96 |
| 3,571,737 | 3/1971 | Miller | 330/4.3 |
| 3,582,820 | 6/1971 | Snitzer | 331/94.5 |
| 3,753,145 | 8/1973 | Chesler | 372/75 |
| 3,808,549 | 4/1974 | Maurer | 331/94.5 |
| 4,233,570 | 11/1980 | Emmett et al. | 372/41 |
| 4,284,962 | 8/1981 | Esterowitz et al. | 372/41 |
| 4,381,141 | 4/1983 | Sakuragi et al. | 350/96.34 |
| 4,464,761 | 8/1984 | Alfano et al. | 372/41 |
| 4,538,278 | 8/1985 | Gergely | 372/70 |
| 4,653,056 | 3/1987 | Baer et al. | 372/27 |
| 4,665,529 | 5/1987 | Baer et al. | 372/107 |
| 4,686,979 | 8/1987 | Gruen et al. | 128/303.1 |
| 4,756,003 | 7/1988 | Baer et al. | 372/75 |

FOREIGN PATENT DOCUMENTS 0214712 3/1987 European Pat. Off. ......... 128/303.1

OTHER PUBLICATIONS

G. J. Kintz et al., "CW and Pulsed 2.8 μm Laser Emission From Diode-Pumped $Er^{3+}$:LiYF$_4$ at Room Temperature," *Appl. Phys. Lett.* 50(22), Jun. 1, 1987, pp. 1553–1555.

*Primary Examiner*—Max Hindenburg
*Attorney, Agent, or Firm*—Wolf, Greenfield & Sacks

[57] ABSTRACT

A laser catheter for insertion in a body passage and for treatment of a relatively inaccessible location with laser radiation in a preselected first wavelength range, typically in the mid-infrared band, that is outside the transmission passband of silica optical fibers. The laser catheter includes an elongated flexible tube, an optical fiber for carrying optical pumping laser radiation in a second wavelength range through the flexible tube, and a laser attached to the flexible tube at or near the distal end thereof and responsive to optical pumping laser radiation in the second wavelength range for generating output laser radiation in the first wavelength range. The laser can comprise a cylindrical laser crystal attached to the distal end of the flexible tube and having laser mirrors on opposite end faces thereof. The laser crystal can be a suitable host material doped with a rare earth ion selected to produce the desired output wavelength. A preferred laser crystal is erbium-doped YAG, which produces an output at 2.94 micrometers. The optical pumping radiation is supplied from an external pump laser, which is preferably an alexandrite laser operating in the wavelength range of 0.7 to 0.8 micrometer.

45 Claims, 2 Drawing Sheets

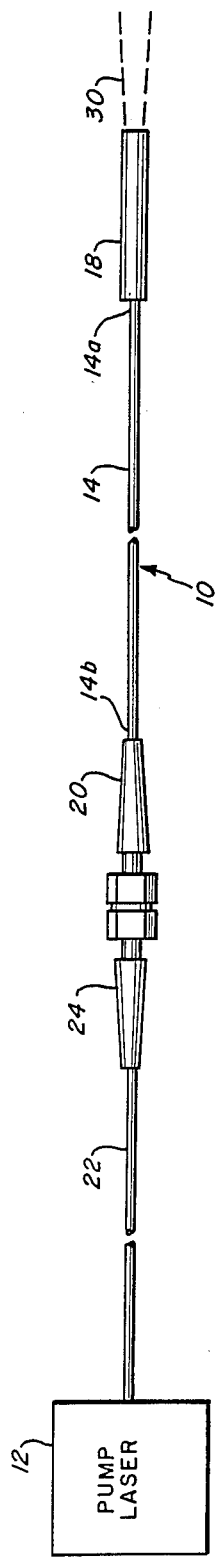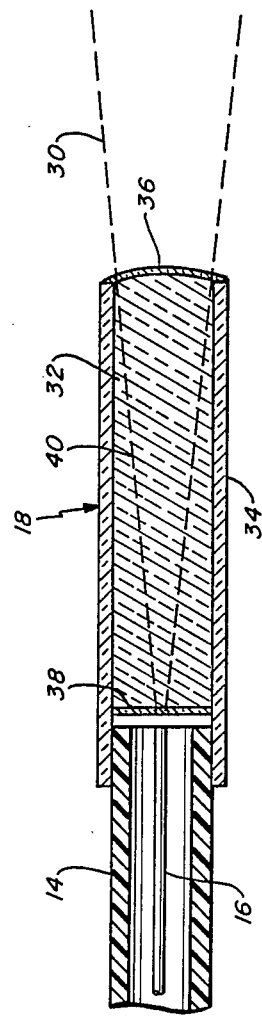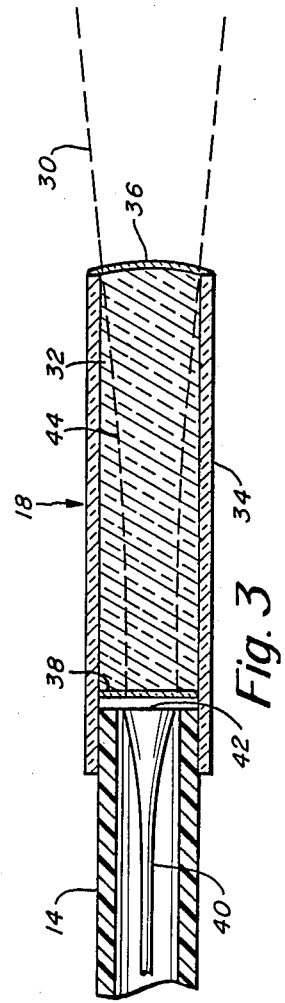

LASER TIPPED CATHETER

FIELD OF THE INVENTION

This invention relates to methods and apparatus for treatment of internal sites within the human body with radiation of a prescribed wavelength and, more particularly, to a catheter having an optically pumped laser or a nonlinear crystal at the distal end for generating radiation at the prescribed wavelength.

BACKGROUND OF THE INVENTION

Laser radiation has been widely used in recent years for various treatment procedures including surgical cutting, vaporization of plaque in arteries, tissue ablation, coagulation, heating and tissue repair. In some cases, the laser radiation is applied externally, while in other cases the laser radiation is applied to a relatively inaccessible internal location. For internal application of laser radiation, laser catheters have been utilized. A conventional laser catheter includes an optical fiber which passes through a thin, flexible tube. The catheter is advanced through an artery or other body passage to a selected internal treatment location. Laser radiation from an external source is transmitted through the optical fiber to the selected internal location.

The selection of laser wavelength for a particular treatment depends on the requirements of the treatment, including depth of penetration, heating effects, treatment area and the like. Recent research in laser-tissue interactions has indicated the desirability of using mid-infrared wavelengths of about 3 micrometers for procedures such as ablation of myocardial tissue, vaporization of plaque in arteries, shallow coagulation and the like. The shallow penetration of these wavelengths allows clean holes, minimal trauma to the surrounding tissue and minimal particulate size. The most highly absorbed wavelength is approximately 2.94 micrometers which is, coincidentally, the exact output wavelength of the erbium-doped YAG laser. Although the erbium-doped YAG laser is easy to fabricate, the catheter delivery system for its output wavelength is not straightforward. The most commonly-used optical fiber is made of silica, which has a passband in the wavelength range of approximately 0.3 to 2.3 micrometers. Laser radiation outside this passband, including the mid-infrared range, is highly absorbed by silica and is not transmitted through the fiber.

It is known that zirconium fluoride optical fibers can be utilized for transmission of wavelengths in the mid-infrared band. However, fibers of this type have only recently become available and have numerous disadvantages including high cost, lack of mechanical strength, susceptibility to damage by high energy laser beams, a slightly hydroscopic nature and potential toxicity when the fiber is exposed to the human body.

A solid state laser having a miniaturized, quick-disconnect laser head is disclosed in U.S. Pat. No. 4,665,529 issued May 12, 1987 to Baer et al. Pumping radiation from a laser diode is carried through an optical fiber to the laser head. A neodymium YAG laser head, which has an output at 1.06 micrometers, is disclosed. The laser output is passed through a frequency doubler crystal. A high efficiency neodymium YAG laser pumped by a laser diode is disclosed in U.S. Pat. No. 4,653,056 issued Mar. 24, 1987 to Baer et al. In U.S. Pat. No. 4,538,278 issued Aug. 27, 1985 to Gergeley, a source of linearly polarized light at a wavelength of about 550–1100 nanometers supplies light through an optical fiber to a nonlinear crystal at the other end of the fiber. The crystal increases the frequency of the light from the source and provides light in the 250–550 nanometer wavelength range. Laser emission at 2.8 micrometers from an erbium-doped $LiYF_4$ crystal is disclosed by G. J. Kintz et al in *Appl. Phys. Lett.* 50(22), June 1, 1987, pp. 1553–1555. The authors suggest pumping of the laser crystal with a laser diode array or with an alexandrite laser and suggest that the disclosed laser may have medical applications.

It is a general object of the present invention to provide improved methods and apparatus for medical treatment with laser radiation.

It is another object of the present invention to provide methods and apparatus for treatment of relatively inaccessible locations in the human body with laser radiation in the mid-infrared band.

It is a further object of the present invention to provide methods and apparatus for treatment of relatively inaccessible locations in the human body with radiation outside the passband of silica optical fibers.

It is yet another object of the present invention to provide a catheter having a laser at the distal end thereof.

It is still another object of the present invention to provide methods and apparatus for treatment of relatively inaccessible locations in the human body with laser radiation in the mid-infrared band while utilizing a silica fiber for transmission of laser radiation to the inaccessible location.

SUMMARY OF THE INVENTION

According to the present invention, these and other objects and advantages are achieved in a catheter for insertion in a body passage or cavity and for treatment with radiation in a first wavelength range. The catheter comprises an elongated tube having a distal end and a proximal end, optical waveguide means for carrying radiation in a second wavelength range through the tube and radiation generating means attached to the tube at the distal end thereof and responsive to radiation in the second wavelength range for generating output radiation in the first wavelength range. In one embodiment, the elongated tube is of suitable size and flexibility to be manipulated through a blood vessel.

The optical waveguide means has a prescribed passband for transmission of radiation without substantial attenuation. Although the first wavelength range for treatment can be outside or inside the passband of the optical waveguide means, the second wavelength range must be within the prescribed passband and is transmitted through the optical waveguide means. Preferably, the optical waveguide means is a silica optical fiber.

According to one aspect of the invention, the radiation generating means is a laser means. The laser means can comprise a laser crystal having an output wavelength in the first wavelength range. The laser crystal can be a suitable host material doped with a rare earth ion selected to produce the desired output wavelength. The laser crystal can be optically pumped by laser radiation in the 0.7 to 0.8 micrometer range, preferably from an alexandrite laser or a laser diode. In a preferred embodiment, the laser crystal is erbium-doped YAG or holmium-doped YAG for producing laser radiation in the mid-infrared band.

In one preferred embodiment, a cylindrical laser crystal has mirrors formed on opposite end faces thereof and is mounted to the tube in coaxial alignment therewith so that radiation carried through the optical fiber is coupled through one end face of the laser crystal and initiates lasing at the desired output wavelength.

In another preferred embodiment, the laser means comprises an annular laser crystal having inner and outer cylindrical surfaces with mirrors formed thereon, and the laser crystal is mounted to the tube in coaxial alignment therewith. The catheter further includes means for redirecting radiation carried through the optical fiber to the inner cylindrical surface of the laser crystal. The laser crystal provides laser radiation in the first wavelength range through the outer cylindrical surface of the annular laser crystal. The redirecting means can be a tapered optical fiber or a reflecting surface.

According to another aspect of the invention, the radiation generating means is a nonlinear crystal for changing the frequency of the radiation carried through the optical fiber to radiation in the first wavelength range. In a preferred embodiment, the nonlinear crystal is lithium niobate responsive to laser radiation at wavelengths of 0.85 micrometer and 1.06 micrometers for generating radiation at 4.26 micrometers.

According to yet another aspect of the invention, there is provided a method for treatment of a selected body location with radiation in a selected first wavelength range. The method comprises the steps of advancing a catheter containing an optical fiber through a body vessel to the vicinity of the selected location, transmitting radiation in a second wavelength range through the optical fiber to the vicinity of the selected location, and generating radiation in the first wavelength range for treatment of the selected location. The step of generating radiation in the first wavelength range is carried out in the vicinity of the selected location in response to radiation in the second wavelength range transmitted through the optical fiber.

BRIEF DESCRIPTION OF THE DRAWINGS

For a better understanding of the present invention together with other and further objects, advantages and capabilities thereof, reference is made to the accompanying drawings which are incorporated herein by reference and in which:

FIG. 1 is a fragmented illustration of a laser catheter in accordance with the present invention and a pump laser for energizing the laser catheter;

FIG. 2 is an enlarged, cross-sectional view of the distal end of the laser catheter of FIG. 1; and FIG. 3 is an enlarged, cross-sectional view of the distal end of the laser catheter illustrating a tapered optical fiber;

DETAILED DESCRIPTION OF THE INVENTION

Figure 4:
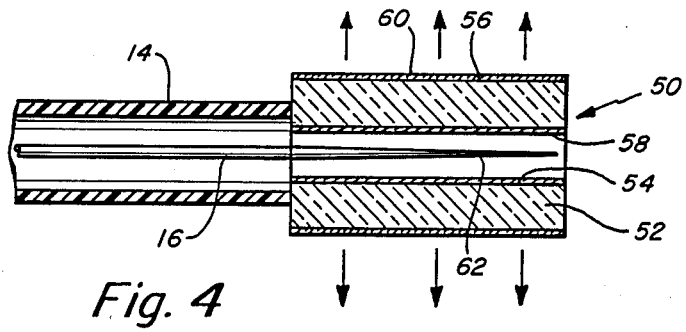
FIG. 4 is an enlarged, cross sectional view of the distal end of the laser catheter illustrating an annular laser crystal and a tapered optical fiber.

A laser catheter 10 in accordance with the present invention and a pump laser 12 for energizing catheter 10 are illustrated in FIG. 1. Laser catheter 10 includes an elongated tube 14 having a distal end 14a and a proximal end 14b. The tube 14 is usually flexible so that it can easily be manipulated through a body passage such as a blood vessel. An optical fiber 16 (FIG. 2) passes through a lumen in tube 14 from the proximal end 14b to the distal end 14a. The optical fiber 16 can pass through a preformed lumen in tube 14 or can be embedded in the tube. A laser 18 is attached to the tube 14 at or near the distal end thereof. An optical fiber connector 20 is attached to the proximal end of optical fiber 16. Laser radiation from pump laser 12 is coupled through an optical fiber 22 to an optical fiber connector 24 which mates with connector 20. Alternatively, the laser radiation from pump laser 12 can be coupled to optical fiber 16 by another suitable optical coupling technique.

The flexible tube 14 and the laser 18 are sufficiently small in diameter that they can be advanced through a body passage, such as a blood vessel, or inserted in a body cavity, to a selected treatment site. The laser 18 is not necessarily the same diameter as tube 14. However, it must be sufficiently small to pass into and through the body passage or body cavity of interest.

In operation, the tube 14 carrying laser 18 is advanced through the body passage to the selected treatment site. The output radiation from laser 18 is in a first wavelength range selected to optimize the treatment procedure. Preferably, the first wavelength range is between about 1.0 and 3.5 micrometers. Examples of treatment procedures using this wavelength range include ablation of myocardial tissue, vaporization of plaque in arteries, shallow coagulation and the like. It will be understood that the invention is not limited to the wavelength range specified above.

The laser 18 is energized by laser radiation in a second wavelength range generated by pump laser 12 and carried by optical fiber 22 and optical fiber 16 to laser 18. The laser 18 is energized by well-known optical pumping techniques, wherein molecules of the laser material are raised to more energetic states by laser radiation in the second wavelength range. The molecules then decay from the energetic states to states of lower energy and emit coherent laser radiation in the first wavelength range. The energy supplied to laser 18 in the second wavelength range must be sufficient to initiate and sustain lasing. The laser 18 can be designed for continuous or pulsed operation, depending on the application. An output laser beam 30 from laser 18 in the first wavelength range can be concentrated or can be spread over a desired volume.

An enlarged cross sectional view of the distal end of tube 14 and of laser 18 in accordance with one embodiment of the invention is shown in FIG. 2. A generally cylindrical laser crystal 32 is mounted in an outer shell 34 which can, for example, be glass or a transparent crystal. A portion of outer shell 34 slides over the distal end of tube 14 and is attached thereto by cement or other conventional means. Preferably, the shell 34 is transparent and an ultraviolet curable cement is used. A mirror 36 is deposited on a distal end face of cylindrical laser crystal 32, and a mirror 38 is deposited on a proximal end face of laser crystal 32. The mirrors 36 and 38 are permanently aligned so as to define a lasing region 40 between them as known in the art. The mirrors 36 and 38 can be formed by well-known dielectric coatings selected to provide a desired transmission characteristic.

Each of the mirrors 36, 38 can be flat or curved so as to define a lasing region having a desired size and shape. In a preferred embodiment, mirror 38 is flat, and mirror 36 is curved so that the lasing region 40 within laser crystal 32 has an approximately conical shape. An apex of conical lasing region 40 is aligned with optical fiber 16 so that laser radiation in the second wavelength range from pump laser 12 is efficiently coupled from optical fiber 16 to laser 18. The mirror 36 at the distal end of laser crystal 32 can be the output window of the laser catheter 10. Alternatively, the laser beam 30 can be supplied through a separate output window (not shown) at the distal end of the catheter.

For proper operation of laser 18, mirror 38 must pass substantially all of the laser radiation supplied from pump laser 12 and must reflect substantially all of the laser radiation generated by laser 18. Mirror 36 must reflect substantially all of the laser radiation supplied from pump laser 12 and must pass a specified fraction, typically in the range of 90-100 percent, of the output laser radiation. As noted above, known dielectric coatings can be selected to provide the desired transmission characteristic as a function of wavelength.

The laser crystal 32 is preferably selected from a variety of rare earth ions in a suitable host material such as yttrium aluminum garnet (YAG), yttrium lithium fluoride (YLF) or yttrium scandium gadolinium garnet (YSGG). The selected rare earth ion depends on the desired output wavelength. In a preferred embodiment, the laser crystal 32 is erbium-doped YAG having an output wavelength of 2.94 micrometers or holmium doped YAG having an output wavelength of 2.06 micrometers. Preferably, the optical fiber 16 is silica for low cost, nontoxicity and flexibility, and the laser crystal 32 is optically pumped by laser radiation in the 0.7 to 0.8 micrometer range.

A preferred pump laser 12 for producing radiation in the 0.7 to 0.8 micrometer range is an alexandrite laser. However, other tunable pump laser sources, including laser diodes, can be utilized. A number of different rare earth ion lasers can be optically pumped by laser radiation in the 0.7 to 0.8 micrometer range. Therefore, one type of tunable pump laser 12 can advantageously be utilized for energizing a number of different laser types. A fixed wavelength pump laser is suitable for use with a particular laser crystal type. The required energy level for the pump laser 12 is typically about one joule per pulse. In an example of the present invention, the laser crystal 32 is a cylindrical erbium-doped YAG crystal having a length of 2 millimeters and a diameter of 1.5 millimeters.

A configuration that provides efficient pumping of the laser is illustrated in FIG. 3. The laser 18 is coupled to the distal end of flexible tube 14 in the same manner as shown in FIG. 2 and described above. An optical fiber 40 passes through tube 14 and has its distal end 42 aligned with mirror 38 so that laser radiation from pump laser 12 is coupled into laser 18. A section of optical fiber 40 near its distal end 42 is gradually increased in diameter so that the end face of fiber 40, which couples laser radiation into laser 18, is larger in diameter than the remainder thereof. The purpose of this configuration is to match the radiation pattern at the distal end of optical fiber 40 to a lasing 44 region in laser crystal 32, thereby providing efficient optical pumping of laser 18.

An alternative embodiment of the present invention is illustrated in FIG. 4. A laser 50 is mounted at the distal end of flexible tube 14. A laser crystal 52 has an annular shape with a cylindrical inside surface 54 and a cylindrical outside surface 56. Laser mirrors 58 and 60 are disposed on surfaces 54 and 56, respectively. The optical fiber 16 is terminated in a diffusing tip 62 such as a tapered optical fiber located within the annular laser crystal 52 for directing pump laser radiation carried through optical fiber 16 outwardly through mirror 58 and into laser crystal 52. The pump laser radiation in the second wavelength range carried by optical fiber 16 optically pumps laser 50, and causes generation of output laser radiation in the first wavelength range. The output laser radiation is directed radially outward through mirror 60. The configuration of FIG. 4 provides output laser radiation having a generally cylindrical pattern, which can be utilized, for example, for heating or vaporizing plaque in an artery. The laser 50 shown in FIG. 4 can, if desired, be mounted in an inflatable balloon for simultaneous application of pressure and radiation.

The pump laser radiation carried through optical fiber 16 can be directed through mirror 58 by a tapered optical fiber located inside the annular laser crystal 52. It is known in the art that a tapered optical fiber causes light to be gradually directed outwardly since the critical angle for reflected rays is gradually exceeded. The fiber 16 which passes through flexible tube 14, can include a section at its distal end that is tapered from full diameter at the point of entry into the laser crystal 52 to essentially zero diameter. Tapering of the optical fiber can be accomplished utilizing hydrofluoric acid as an etchant. The fiber is placed in the etching solution and is withdrawn at a controlled rate which may be constant to produce a conical taper or variable to produce a variable rate of taper. By varying the rate of taper, the light intensity distribution along the axis of the tapered portion can be varied.

Figure 5:
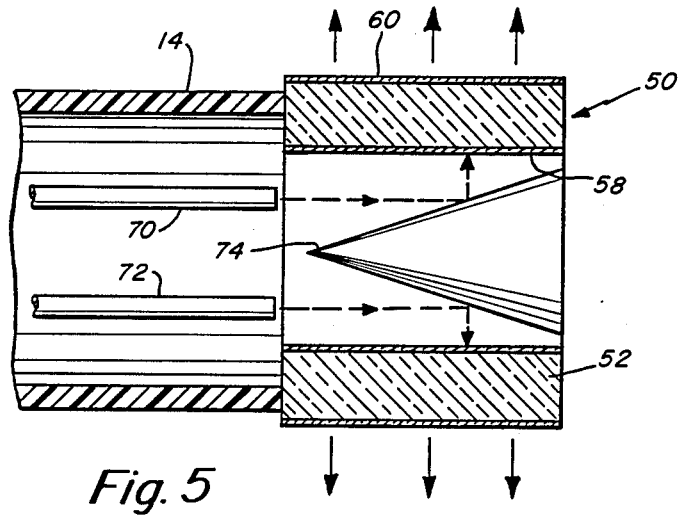
FIG. 5 is an enlarged, cross-sectional view of the distal end of the laser catheter illustrating an annular laser crystal and a reflector.

An alternative configuration for supplying pump laser radiation to an annular laser located at the distal end of a catheter is shown in FIG. 5. Laser 50 including annular laser crystal 52, having laser mirrors 58 and 60 on cylindrical inside and outside surfaces, respectively, is mounted at the distal end of flexible tube 14. A plurality of optical fibers, including fibers 70 and 72, pass through tube 14 and are arranged in a generally circular configuration around the catheter axis. Located within annular laser crystal 52 is a conical mirror 74 having its axis aligned with the axis of the catheter and having its apex directed toward the ends of optical fibers 70, 72. In use, laser radiation from pump laser 12 passes through the plurality of optical fibers 70, 72, etc. and is reflected by conical mirror 74 at approximately right angles to the catheter axis. A cylindrical pattern of laser radiation is directed through mirror 58 into laser crystal 52 for optical pumping thereof so as to produce lasing. The laser crystal provides laser radiation at the desired output wavelength through mirror 60.

In some cases, it is desirable to use a guidewire to assist in advancing a catheter through a blood vessel or other body passage to a treatment site. One configuration of the present invention suitable for use with a guidewire, is a catheter tube having a lumen for passage of a guidewire and one or more optical fibers positioned around the guidewire. Each optical fiber is terminated in a laser of smaller diameter than would otherwise be used. The guidewire is used to advance the catheter to the treatment site, and then the laser, or lasers, surrounding the guidewire are energized to provide the desired treatment.

It will be understood that numerous variations are included within the scope of the present invention. The laser positioned at or near the distal end of the catheter can have any suitable size or shape which will pass through the body passage and which will provide the desired laser wavelength and energy level. The output laser radiation can be at any selected wavelength and can be concentrated, diffused or have any other desired spatial distribution. It can be pulsed or continuous. Different materials can be utilized in the laser to provide different output wavelengths and operating characteristics. All that is required is that the output wavelength provided by the laser be selected as suitable for the desired treatment procedure, while the pump wavelength transmitted through the catheter be within the passband of the optical fiber and be suitable for optical pumping of the laser. Thus, there is provided methods and apparatus for treating relatively inaccessible locations with laser radiation of a selected wavelength, even though that wavelength is not easily transmitted through an optical fiber to the inaccessible location.

The catheter of the present invention can incorporate additional functions when desired, including an inflatable balloon, means for flushing the body passage with a fluid, means for viewing the body passage, etc. The laser can be positioned within a balloon so that outward pressure is applied to a body passage during laser radiation. This treatment can be used for treatment of plaque in arteries. The catheter can include two or more optical fibers each coupled to a laser at the distal end of the catheter for increased energy output. The lasers can be energized at the same or different times.

Figure 6:
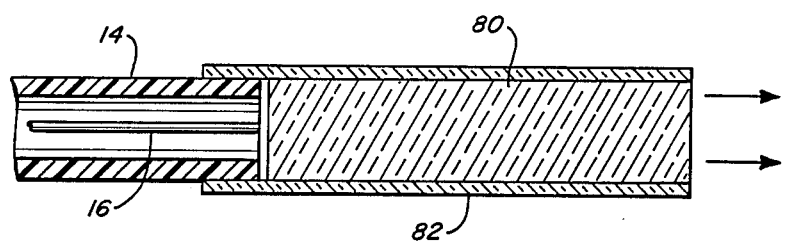
FIG. 6 is an enlarged, cross-sectional view of the distal end of a catheter incorporating a nonlinear crystal, in accordance with another embodiment of the present invention.

In some cases, it may be desirable to replace the laser at the distal end of the catheter with a nonlinear crystal for changing the frequency of the radiation supplied through the optical fiber. Referring to FIG. 6, a nonlinear crystal 80 is mounted at the distal end of flexible tube 14. The crystal 80 has a cylindrical shape and is axially aligned with the optical fiber 16 that passes through tube 14. A glass shell or tube 82 surrounds crystal 80, and the proximal end of shell 82 is secured to the distal end of tube 14. In operation, laser radiation at one or more wavelengths is transmitted through optical fiber 16 to crystal 80. The nonlinear crystal 80 produces output radiation at a different wavelength from the wavelengths carried through optical fiber 16. Nonlinear crystals are known in the art and can be selected for compatibility with the desired input and output wavelengths.

In a preferred embodiment, the crystal 82 is lithium niobate. Laser radiation at a wavelength of 1.06 micrometers from a neodymium YAG laser and laser radiation at a wavelength of 0.85 micrometer from a laser diode are supplied simultaneously through the optical fiber 16 to crystal 80. The lithium niobate crystal produces output radiation at 4.26 micrometers. The radiation at 4.26 micrometers is useful in measuring carbon dioxide concentration in the blood and, as noted above, cannot be transmitted through a silica optical fiber. It will be understood that by the selection of other input wavelengths and crystal materials, different output wavelengths can be provided.

While there has been shown and described what is at present considered the preferred embodiments of the present invention, it will be obvious to those skilled in the art that various changes and modifications may be made therein without departing from the scope of the invention as defined by the appended claims.

What is claimed is:

1. A laser catheter for internal application of laser radiation in a first wavelength range, comprising:
   an elongated, flexible element suitable for insertion in a body passage or cavity, said flexible element having a distal end and a proximal end;
   optical waveguide means for carrying laser radiation in a second wavelength range through said flexible element; and
   laser means attached to said flexible element at the distal end thereof and suitable for insertion in a body passage or cavity, said laser means being responsive to laser radiation in said second wavelength range carried by said optical waveguide means, for generating laser radiation in said first wavelength adjacent to an internal application site.

2. A laser catheter as defined in claim 1 wherein said optical waveguide means comprises a silica optical fiber having a prescribed passband for transmission of laser radiation without substantial attenuation and wherein said second wavelength range is within said prescribed passband.

3. A laser catheter as defined in claim 2 wherein said laser means comprises a laser crystal mounted to said flexible element, said laser crystal being capable of generating laser radiation in the mid-infrared band of wavelengths in response to optical pumping radiation in the 0.7 to 0.8 micrometer band of wavelengths.

4. A laser catheter as defined in claim 3 wherein said laser crystal comprises an erbium-doped host material selected from the group consisting of YAG, YLF and YSGG.

5. A laser catheter as defined in claim 3 wherein said laser crystal comprises a holmium-doped host material selected from the group consisting of YAG, YLF and YSGG.

6. A laser catheter as defined in claim 3 further including a laser source coupled to the proximal end of said optical fiber for generating laser radiation in said second wavelength range.

7. A laser catheter as defined in claim 6 wherein said laser source comprises an alexandrite laser.

8. A laser catheter as defined in claim 6 wherein said laser source comprises a laser diode.

9. A laser catheter as defined in claim 6 wherein said laser source is tunable over a range of wavelengths.

10. A laser catheter as defined in claim 2 wherein said first wavelength range is in the mid-infrared band of wavelengths.

11. A laser catheter as defined in claim 10 wherein said laser means comprises an annular laser crystal having inner and outer cylindrical surfaces with mirrors thereon, and said laser crystal further including means for redirecting laser radiation carried through said optical fiber to the inner cylindrical surface of said laser crystal, whereby said laser crystal provides laser radiation in said first wavelength range through said outer cylindrical surface.

12. A laser catheter as defined in claim 11 wherein said means for redirecting laser radiation comprises a reflecting surface within said annular laser crystal.

13. A laser catheter as defined in claim 12 wherein said reflecting surface has a conical shape.

14. A laser catheter as defined in claim 11 wherein said means for redirecting laser radiation comprises a section of said optical fiber within said annular laser crystal that is tapered to a smaller diameter than the remainder of said optical fiber.

15. A laser catheter as defined in claim 10 wherein said laser means comprises a cylindrical laser crystal having mirrors on opposite end faces thereof so as to produce a stable lasing cavity, said laser crystal being mounted to said flexible element so that laser radiation carried through said optical fiber is coupled through one end face of said laser crystal.

16. A laser catheter as defined in claim 15 wherein said laser crystal comprises a host material doped with a rare earth ion for providing laser radiation in a wavelength range between 1.0 and 3.5 micrometers.

17. A laser catheter as defined in claim 15 wherein said laser crystal includes a flat mirror on a proximal end face thereof and a curved mirror on a distal end face thereof.

18. A laser catheter as defined in claim 15 including matching means for efficiently coupling laser radiation in said second wavelength range to said laser crystal by substantially matching the radiation pattern from said optical fiber to a lasing region in said laser crystal.

19. A laser catheter as defined in claim 18 wherein said matching means comprises a section of said optical fiber near the distal end thereof adjacent to said laser crystal that is tapered to a larger diameter than the remainder of said optical fiber.

20. A laser catheter as defined in claim 1 wherein said second wavelength range is 0.7 to 0.8 micrometer and said first wavelength range is 1.0 to 3.5 micrometers.

21. A laser catheter as defined in claim 1 wherein said flexible element has a suitable size and flexibility for manipulation through a blood vessel.

22. A laser catheter as defined in claim 1 wherein said optical waveguide means has a prescribed passband for transmission of laser radiation without substantial attenuation and wherein said second wavelength range is within said prescribed passband.

23. Apparatus for internal treatment with radiation in a selected first wavelength range, comprising:
an elongated, flexible tube for insertion in a body passage or cavity, said tube having a distal end and a proximal end;
optical waveguide means for carrying laser radiation in a second wavelength range through said tube; and
means for generating radiation in said first wavelength range adjacent to an internal treatment site, said generating means being affixed to said tube at the distal end thereof and being responsive to radiation in said second wavelength range carried through said optical waveguide means.

24. Apparatus as defined in claim 23 wherein said optical waveguide means comprises a silica optical fiber.

25. Apparatus as defined in claim 24 wherein said generating means comprises a laser and wherein radiation in said second wavelength range is coupled from said optical fiber to said laser for optical pumping thereof.

26. Apparatus as defined in claim 25 wherein said first wavelength range s in the mid-infrared band.

27. Apparatus as defined in claim 25 wherein said laser comprises a cylindrical laser crystal having mirrors on opposite end faces thereof, said laser crystal being mounted to said tube so that laser radiation carried through said optical fiber is coupled to one end face of said laser crystal.

28. Apparatus as defined in claim 25 wherein said laser comprises an annular laser crystal having inner and outer cylindrical surfaces with mirrors thereon, and further including means for redirecting laser radiation carried through said optical fiber to the inner cylindrical surface of said laser crystal, whereby said laser crystal provides laser radiation in said first wavelength range through said outer cylindrical surface.

29. Apparatus as defined in claim 24 wherein said generating means comprises a nonlinear crystal selected to convert radiation in said second wavelength range to radiation in said first wavelength range.

30. Apparatus as defined in claim 29 wherein said nonlinear crystal comprises lithium niobate responsive to laser radiation at wavelengths of 0.85 micrometer and 1.06 micrometers for generating radiation at 4.26 micrometers.

31. Apparatus as defined in claim 29 wherein said nonlinear crystal comprises lithium niobate.

32. A method for treatment of a selected internal body location with radiation in a selected first wavelength range, comprising the steps of:
advancing a catheter containing an optical waveguide through a body passage or cavity to the vicinity of the selected location;
transmitting radiation in a second wavelength range through said optical waveguide to the vicinity of the selected location; and
generating radiation in said first wavelength range for treatment of the selected location, said generating step being carried out in the vicinity of the selected location in response to radiation in said second wavelength range transmitted through said optical waveguide.

33. A treatment method as defined in claim 32 wherein the step of transmitting radiation in a second wavelength range includes the step of transmitting radiation through a silica optical fiber.

34. A treatment method as defined in claim 33 wherein the step of generating radiation in said first wavelength range includes the step of generating laser radiation with a laser attached to said catheter at or near the distal end thereof.

35. A treatment method as defined in claim 34 wherein the step of generating laser radiation includes the step of generating laser radiation in the mid-infrared band of wavelengths.

36. A treatment method as defined in claim 34 wherein the step of generating laser radiation includes the steps of
providing a generally cylindrical laser crystal having laser mirrors on opposite end faces thereof, and
coupling radiation in said second wavelength range from said optical fiber through one end face of said laser crystal for optical pumping thereof.

37. A treatment method as defined in claim 34 wherein the step of generating laser radiation includes the steps of
providing an annular laser crystal having inner and outer cylindrical surfaces with laser mirrors thereon, and redirecting laser radiation in said second wavelength range from said optical fiber to the inner cylindrical surface of said annular laser crystal for optical pumping thereof.

38. A catheter assembly for internal treatment with radiation in a first wavelength range, comprising:
   an elongated, flexible catheter adapted for insertion in a body passage or cavity, said catheter having a distal end and a proximal end;
   optical waveguide means for carrying radiation in a second wavelength range through said catheter; and
   means attached to said catheter at the distal end thereof and responsive to radiation in said second wavelength range for generating radiation in said first wavelength range adjacent to an internal treatment site.

39. A catheter assembly as defined in claim 38 wherein said means for generating radiation comprises laser means.

40. A catheter assembly as defined in claim 39 wherein said optical waveguide means comprises an optical fiber having a prescribed passband for transmission of radiation and wherein said second wavelength range is within said prescribed passband.

41. A catheter assembly as defined in claim 40 wherein said catheter comprises an elongated, flexible tube.

42. A catheter assembly as defined in claim 41 wherein said laser means comprises a laser crystal having mirrors on opposite end faces thereof so as to produce a stable lasing cavity, said laser crystal being mounted to said flexible tube so that radiation carried through said optical fiber is coupled through one end face of said laser crystal.

43. A catheter assembly as defined in claim 42 wherein said laser crystal comprises a host material doped with a rare earth ion for providing laser radiation in a wavelength range between 1.0 and 3.5 micrometers.

44. A catheter assembly as defined in claim 38 wherein said first wavelength range is in the mid-infrared band of wavelengths.

45. A catheter assembly as defined in claim 38 wherein said means for generating radiation comprises a nonlinear crystal.

* * * * *